US011423533B2

(12) United States Patent
Kemmochi et al.

(10) Patent No.: US 11,423,533 B2
(45) Date of Patent: Aug. 23, 2022

(54) IMAGE PROCESSING METHOD AND IMAGE PROCESSING SYSTEM

(71) Applicant: Konica Minolta, Inc., Tokyo (JP)

(72) Inventors: Hiroaki Kemmochi, Hachioji (JP); Yasuyuki Motokui, Kunitachi (JP); Noboru Koyama, Niiza (JP)

(73) Assignee: KONICA MINOLTA, INC., Tokyo (JP)

(*) Notice: Subject to any disclaimer, the term of this patent is extended or adjusted under 35 U.S.C. 154(b) by 103 days.

(21) Appl. No.: 16/472,439

(22) PCT Filed: Dec. 18, 2017

(86) PCT No.: PCT/JP2017/045257
§ 371 (c)(1),
(2) Date: Jun. 21, 2019

(87) PCT Pub. No.: WO2018/123677
PCT Pub. Date: Jul. 5, 2018

(65) Prior Publication Data
US 2021/0133953 A1    May 6, 2021

(30) Foreign Application Priority Data
Dec. 27, 2016  (JP) .............. JP2016-253698

(51) Int. Cl.
G06K 9/00       (2006.01)
G06T 7/00       (2017.01)
G01N 21/64      (2006.01)

(52) U.S. Cl.
CPC ....... G06T 7/0012 (2013.01); G01N 21/6428 (2013.01); G06T 7/97 (2017.01)

(58) Field of Classification Search
CPC ...... G06T 7/0012; G06T 7/97; G01N 21/6428
See application file for complete search history.

(56) References Cited

U.S. PATENT DOCUMENTS

| 10,175,220 B2* | 1/2019 | Watanabe | G01N 33/4833 |
| 2011/0037846 A1* | 2/2011 | Huang | G01N 33/588 348/79 |
| 2014/0270459 A1* | 9/2014 | Moll | G01N 21/6428 382/134 |

FOREIGN PATENT DOCUMENTS

| EP | 3086110 A1 | 10/2016 |
| JP | 2005164815 A | 6/2005 |

(Continued)

OTHER PUBLICATIONS

International Preliminary Report on Patentability dated Jul. 2, 2019 from corresponding International Application No. PCT/JP2017/045257.

(Continued)

Primary Examiner — Tom Y Lu
(74) Attorney, Agent, or Firm — Lucas & Mercanti, LLP

(57) ABSTRACT

An image processing method includes: a fluorescent image capturing step of capturing a fluorescent image of a fluorescently labeled tissue specimen; a creating step of creating a fluorescent whole slide image based on the captured fluorescent image; and a storing step of storing the created fluorescent whole slide image. The tissue specimen is fluorescently labelled by using, as a staining reagent, fluorescent substance integrated nanoparticles obtained by bonding a biological substance recognition part to fluorescent particles on which a plurality of fluorescent substances are integrated.

8 Claims, 9 Drawing Sheets

(56) References Cited

FOREIGN PATENT DOCUMENTS

| | | | |
|---|---|---|---|
| JP | 2008051772 A | 3/2008 | |
| JP | 2013044967 A | 3/2013 | |
| JP | 2014098575 A | 5/2014 | |
| JP | 2016136104 A | 7/2016 | |
| WO | WO-2015093518 A1 * | 6/2015 | .............. G06T 7/11 |
| WO | 2016080187 A1 | 5/2016 | |

OTHER PUBLICATIONS

Written Opinion of the International Searching Authority dated Mar. 6, 2018 from corresponding International Application No. PCT/JP2017/045257 and English translation.
EPO, Extended European Search Report for the corresponding European patent application No. 17888370.8, dated Nov. 20, 2019 (9 pages).
International Search Report dated Mar. 6, 2018 for PCT/JP2017/045257 and English translation.
JPO, Office Action for the corresponding Japanese patent application No. 2018-559064, dated Nov. 9, 2021, with English translation.
EPO, Office Action for the corresponding European patent application No. 17888370.8, dated Jan. 21, 2022.

* cited by examiner

| ARRANGEMENT NO. | | STAGE COORDINATE | | |
|---|---|---|---|---|
| X-AXIS | Y-AXIS | X-AXIS | Y-AXIS | Z-AXIS |
| 1 | 1 | | | |
| 1 | 2 | | | |
| 1 | 3 | | | |
| ⋮ | ⋮ | ⋮ | ⋮ | ⋮ |

FIG.13

| LABEL | SPOT NO. | | | | | | | |
|---|---|---|---|---|---|---|---|---|
| | 1 | 2 | 3 | 4 | 5 | 6 | 7 | 8 |
| SILICA NANOPARTICLES ENCLOSING Cy5 | − | 4 | 14 | 32 | 120 | 362 | + | + |
| SILICA NANOPARTICLES ENCLOSING TETRAMETHYLRHODAMINE | − | 6 | 12 | 34 | 112 | 380 | + | + |
| SILICA NANOPARTICLES ENCLOSING FITC | − | − | 10 | 36 | 118 | 381 | + | + |
| Cy5 | − | − | − | − | + | + | + | + |
| TETRAMETHYLRHODAMINE | − | − | − | − | + | + | + | + |
| FITC | − | − | − | − | + | + | + | + |

−: THERE ARE NOT ANY BRIGHT SPOTS HAVING A BACKGROUND LEVEL OR MORE.
+: THE BRIGHT SPOT CANNOT BE DISTINGUISHED FROM SURROUNDING BRIGHT SPOTS DUE TO HIGH EMISSION INTENSITY.

FIG.14

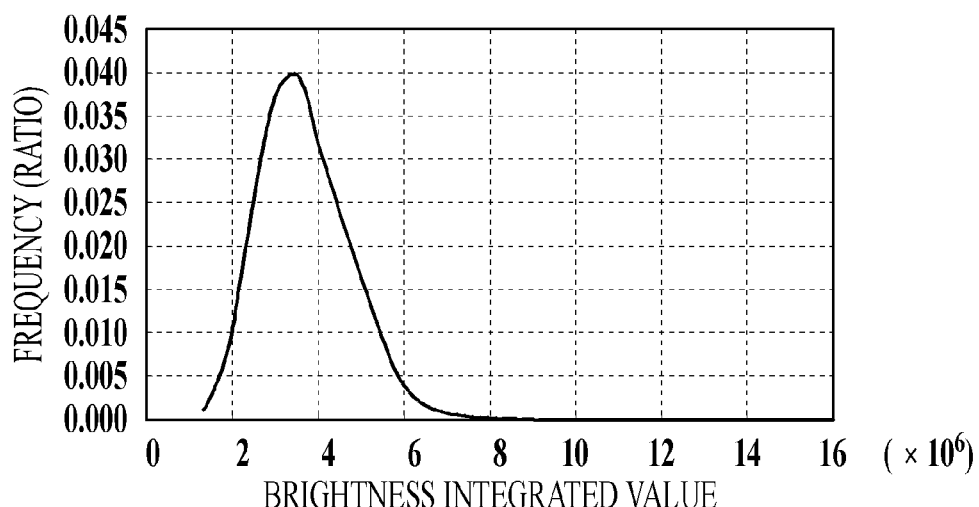

IMAGE PROCESSING METHOD AND IMAGE PROCESSING SYSTEM

CROSS REFERENCE TO RELATED APPLICATION

This Application is a 371 of PCT/JP2017/045257 filed on Dec. 18, 2017 which, in turn, claimed the priority of Japanese Patent Application No. 2016-253698 filed on Dec. 27, 2016, both applications are incorporated herein by reference.

TECHNICAL FIELD

The present invention relates to an image processing method and an image processing system.

BACKGROUND ART

In recent years, much attention has been paid to a virtual microscope as an advanced technology in the field of pathology and the like. The virtual microscope is a system in which an image observed with an optical microscope is converted to digital data and a tissue specimen can be observed on a display as if the optical microscope were actually being used.

In particular, the whole tissue specimen on a slide glass is imaged, and an obtained image is converted to digital data which is stored in a database. The image is observed by using viewer software installed in a personal computer or the like. At this time, the image can be observed while performing operations of up-down and right-left movements, enlargement, reduction and the like in the same manner as in observation using the optical microscope. Therefore, this microscope can be called the virtual microscope. The digital image data of the whole tissue specimen, which is called a whole slide image (WSI), is stored in the database. The stored digital image data can be accessed via the Internet or the like. Consequently, for example, the data can be used for quick pathological diagnosis by a pathologist at a remote location, and a rare tissue specimen can be browsed by anyone.

Additionally, the whole tissue specimen on the slide glass can be imaged by an image processing system called WSI creation system. The WSI creation system includes a microscope device that captures a microscope image, a control unit that creates the WSI based on the captured image, and others. For example, as in Patent Literature 1, partial images on the slide are captured with a scanner, and obtained pieces of partial image data are pasted together to prepare the image data of the whole tissue specimen.

In staining of the tissue specimen that is an observation target, for example, HE staining, immunohistochemical staining such as an oxygen antibody method or a fluorescent antibody method, or the like is used.

In particular, the fluorescent antibody method has been recently often used as a cancer diagnosis method, because an antigen in the tissue specimen can be detected with a high sensitivity. The fluorescent antibody method is a technique of beforehand labeling an antibody with a fluorescent substance, staining a tissue specimen (an antigen-antibody reaction), and then irradiating the tissue specimen with excitation light to emit fluorescence, so that this emission is observed with a fluorescent microscope. In Patent Literature 2, there is disclosed a WSI creation system in which image data of a specimen stained by a fluorescent antibody method is prepared.

CITATION LIST

Patent Literature

Patent Literature 1: Japanese Patent Laid-Open No. 2005-164815
Patent Literature 2: Japanese Patent Laid-Open No. 2008-517772

SUMMARY OF INVENTION

Technical Problem

To achieve observation with a virtual microscope, it is necessary to obtain an image of a tissue specimen at a high resolution, and hence, imaging is performed by using a high-magnification objective lens. An observable field of view is narrow at the high magnification, and hence, the imaging of the whole tissue specimen requires much time.

However, in a case of fluorescent antibody method, a heretofore used fluorescent substance such as a fluorescent dyestuff or a quantum dot has a low light resistance. Therefore, when the substance is irradiated with excitation light for a long time, fading occurs. That is, when the fading occurs due to the irradiation with the excitation light during focusing or the imaging of the whole tissue specimen, any WSI cannot be acquired, and additionally, when the image is analyzed based on the WSI, fluorescent brightness information is impaired, thereby making it difficult to perform quantitative analysis.

The present invention has been developed in view of the above problem, and an object thereof is to provide an image processing method and an image processing system by which an entire image of a specimen can be acquired at a high resolution without fading during imaging in a fluorescent antibody method.

Solution to Problem

To solve the above problem, an image processing method according to claim 1 includes:

a fluorescent image capturing step of capturing a fluorescent image of a fluorescently labeled tissue specimen, a creating step of creating a fluorescent whole slide image based on the captured fluorescent image, and a storing step of storing the created fluorescent whole slide image, wherein the tissue specimen is fluorescently labelled by using, as a staining reagent, fluorescent substance integrated nanoparticles obtained by bonding a biological substance recognition part to fluorescent particles on which a plurality of fluorescent substances are integrated.

In the invention according to claim 2, the image processing method according to claim 1 includes a specifying step of specifying a focus position of the fluorescent image, wherein in the specifying step, a fluorescent bright spot of the fluorescent substance integrated nanoparticles is specified as the fluorescent focus position, and in the fluorescent image capturing step, a focused fluorescent image is captured based on the fluorescent focus position.

In the invention according to claim 3, the image processing method according to claim 2 includes a bright field image capturing step of capturing a bright field image of the tissue specimen, wherein in the specifying step, an arbitrary coordinate on the bright field image is specified as a bright field focus position, and in the fluorescent image capturing step, the focused fluorescent image is captured based on the bright field focus position and the fluorescent focus position.

In the invention according to claim 4, in the image processing method according to any one of claims 1 to 3, wherein the tissue specimen is fluorescently labelled in a multiplied manner by use of the staining reagent in which the fluorescent substance integrated nanoparticles are used, and another staining reagent.

In the invention according to claim 5, in the image processing method according to claim 4, an excitation wavelength and an emission wavelength of the fluorescent substance for use in the other staining reagent do not overlap with an excitation wavelength and an emission wavelength of the fluorescent substance that the fluorescent substance integrated nanoparticles have, respectively.

In the invention according to claim 6, the image processing method according to any one of claims 1 to 5 includes a detection step of detecting a biological substance in the fluorescently labelled tissue specimen, wherein in the detection step, an expression level of the biological substance is obtained by measuring a number of bright spots.

In the invention according to claim 7, the image processing method according to any one of claims 1 to 5 includes a detection step of detecting a biological substance in the fluorescently labelled tissue specimen, wherein in the detection step, an expression level of the biological substance is displayed as a fluorescent brightness map in which intensity of a fluorescent brightness is represented by light and shade of color.

In the invention according to claim 8, the image processing method according to any one of claims 1 to 6 includes a bright field image capturing step of capturing a bright field image of the tissue specimen, wherein the bright field image is obtained by imaging the tissue specimen stained with one or more staining agents with which a specific cell type, a specific region or a specific tissue structure is recognizable.

An image processing system according to claim 9 includes an image capturing unit that captures a fluorescent image of a fluorescently labelled tissue specimen, a creating unit that creates a fluorescent whole slide image based on the fluorescent image captured by the image capturing unit, and a storing unit that stores the fluorescent whole slide image created by the creating unit, wherein the tissue specimen is fluorescently labelled by using, as a staining reagent, fluorescent substance integrated nanoparticles obtained by bonding a biological substance recognition part to fluorescent particles on which a plurality of fluorescent substances are integrated.

Advantageous Effect of Invention

According to the present invention, there can be provided an image processing method and an image processing system by which an entire image of a specimen can be acquired at a high resolution without fading during imaging in a fluorescent antibody method.

BRIEF DESCRIPTION OF DRAWING

FIG. 13 is an explanatory view of effectiveness of a biological substance detection method to which the present invention is applied.

FIG. 14 is a diagram showing a brightness distribution of the fluorescent substance integrated nanoparticles.

DESCRIPTION OF EMBODIMENT

Figure 1:
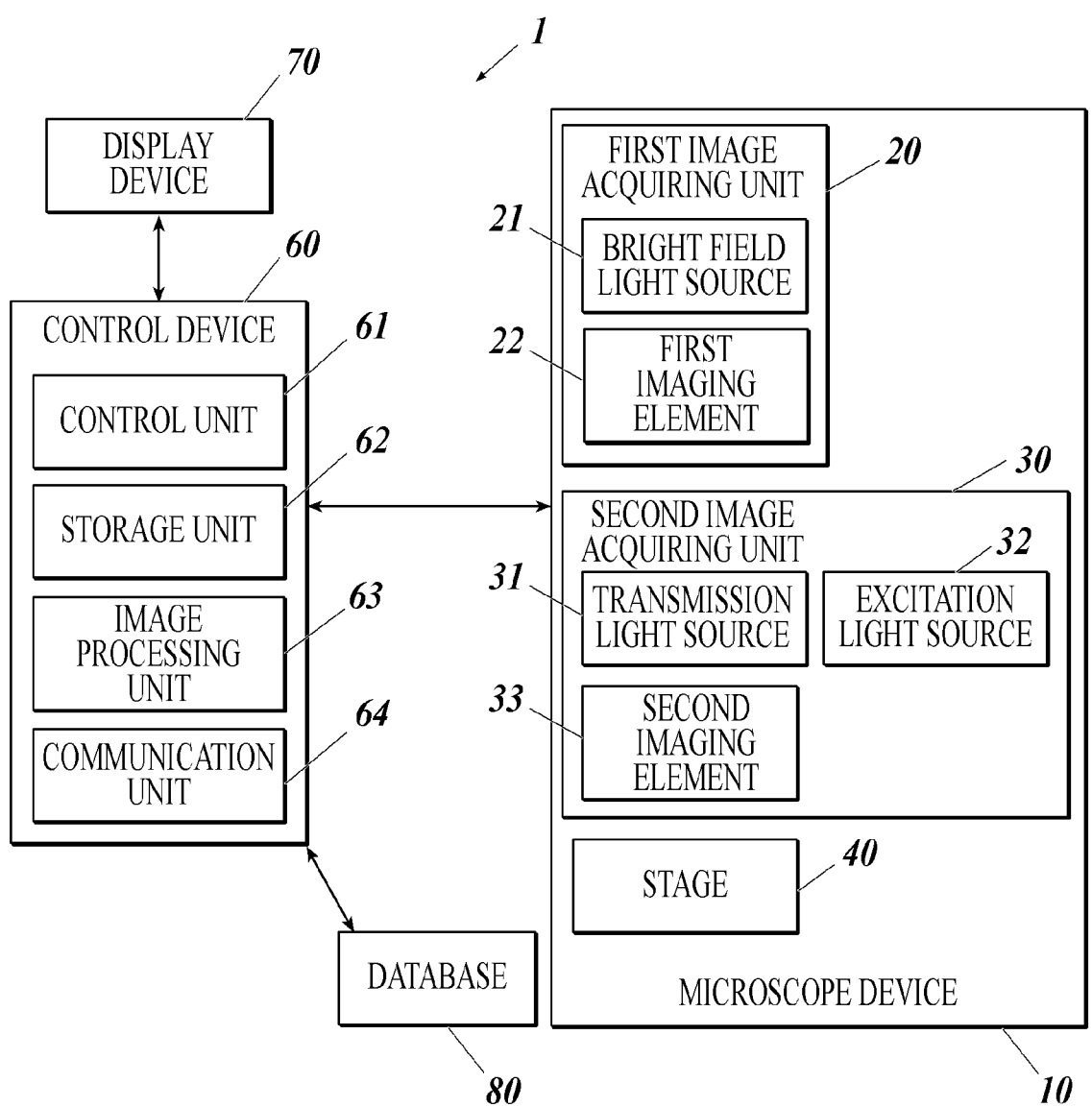
FIG. 1 is a view showing a schematic configuration of an image processing system according to the present invention.

Hereinafter, description will be made as to preferable embodiments of the present invention with reference to the drawing.

[Image Processing System]

FIG. 1 shows a schematic configuration of an image processing system 1 (a WSI creation system) in the present invention. As shown in FIG. 1, the image processing system 1 includes a microscope device 10, a control device 60, a display device 70 and a database 80.

The microscope device 10 includes a first image acquiring unit 20, a second image acquiring unit 30, and a stage 40.

On the stage 40, an immunostained tissue specimen 50 is installed. The tissue specimen 50 is an example of a biological sample.

Figure 2:
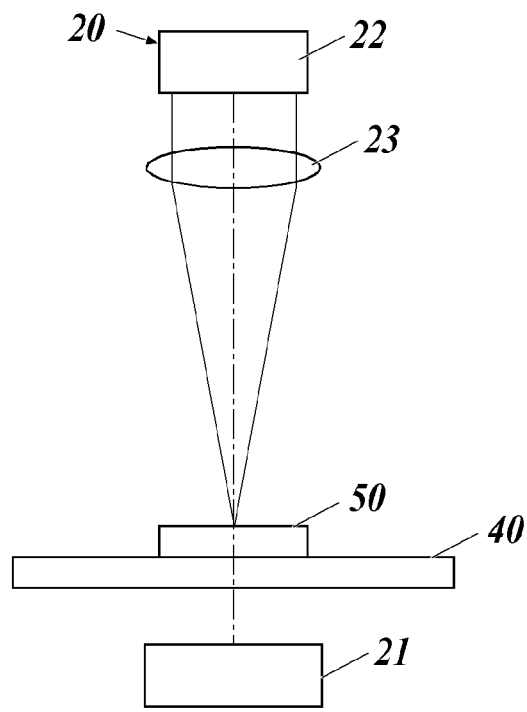
FIG. 2 is a view showing a schematic configuration of a first image acquiring unit.

FIG. 2 shows a schematic configuration of the first image acquiring unit 20.

The first image acquiring unit 20 acquires a bright field image of the tissue specimen 50. The first image acquiring unit 20 includes a bright field light source 21, a first imaging element 22, and a light guide lens 23.

The bright field light source 21 is a light source that irradiates the tissue specimen 50 with light to create an optical image for the acquisition of the bright field image, and is installed to irradiate the stage 40 with light from below. When the tissue specimen 50 is irradiated by the bright field light source 21 to create the optical image, the optical image is guided via the light guide lens 23 to the first imaging element 22, and the bright field image of the tissue specimen 50 is captured by the first imaging element 22.

Note that the first imaging element 22 is an imaging element such as a two-dimensional CCD sensor that is capable of acquiring a two-dimensional image from the optical image of the tissue specimen 50.

Figure 3:
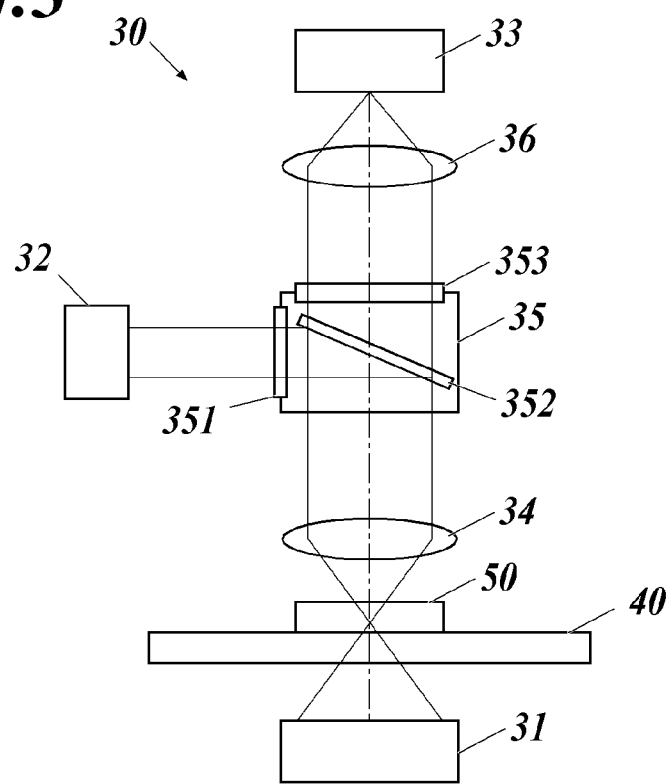
FIG. 3 is a view showing a schematic configuration of a second image acquiring unit.

FIG. 3 shows a schematic configuration of the second image acquiring unit 30.

The second image acquiring unit 30 acquires a fluorescent image of the tissue specimen 50.

The second image acquiring unit 30 includes a transmission light source 31, an excitation light source 32, a second imaging element 33, an objective lens 34, a fluorescent cube 35, and an image forming lens 36. The fluorescent cube 35 includes an excitation filter 351, a dichroic mirror 352 and an absorption filter 353.

The transmission light source 31 is a light source for use in acquiring a transmission observation image of the tissue specimen 50, and is installed to irradiate the stage 40 with the light from below.

The excitation light source 32 is a lamp that emits the excitation light from a light source such as a discharge tube. The excitation filter 351 is a filter that only transmits the excitation light. The dichroic mirror 352 is a mirror that reflects or transmits predetermined-wavelength light as a boundary, and here, the mirror reflects the excitation light and transmits fluorescence. The absorption filter 353 is a filter that cuts off the excitation light and transmits only the fluorescence.

In the second image acquiring unit 30, when the excitation light source 32 is lit, the excitation light passes through the excitation filter 351, is reflected by the dichroic mirror 352, and passes through the objective lens 34 to irradiate the tissue specimen 50. As a result, the fluorescence is emitted from the tissue specimen 50, and the fluorescence is condensed by the objective lens 34 to pass through the dichroic mirror 352 and the absorption filter 353. Afterward, the fluorescence is guided as the fluorescent image via the image forming lens 36 to the second imaging element 33, and the image is captured by the second imaging element 33. Note that the objective lens 34 includes a low magnification objective lens (e.g., 20 times) and a high magnification objective lens (e.g., 40 times).

The second imaging element 33 is an imaging element such as a one-dimensional CCD camera that is capable of capturing a one-dimensional image or a two-dimensional image in a longitudinal direction that is a predetermined direction, and the element can acquire the fluorescent image of the tissue specimen 50 at a high resolution.

The microscope device 10 is connected to the control device 60 that controls these components. The control device 60 includes a control unit 61, a storage unit 62, an image processing unit 63 and a communication unit 64.

The control unit 61 includes a central processing unit (CPU), a random access memory (RAM) and others. The control unit executes various types of processing by cooperation with various programs stored in the storage unit 62, and comprehensively controls an operation of the microscope device 10.

The control unit 61 is connected to the stage 40, and controls raising and lowering of the stage 40, so that a focus position (Z-coordinate) of the tissue specimen 50 installed on the stage 40 can be controlled. Furthermore, the control unit 61 is connected to the first image acquiring unit 20, and controls the bright field light source 21 and the first imaging element 22 to capture the bright field image. Additionally, the control unit 61 is connected to the second image acquiring unit 30, and controls the transmission light source 31, the excitation light source 32, and the second imaging element 33 to capture the fluorescent image.

The storage unit 62 includes a nonvolatile memory such as a hard disk drive (HDD) or a semiconductor, and others. The storage unit 62 stores a program to perform the bright field image capturing and the fluorescent image capturing.

The image processing unit 63 performs image processing of the fluorescent image captured by the microscope device 10, and creates a whole slide image (WSI). As described later, in accordance with an instruction of the control unit 61, captured partial images are synthesized to create an entire image of the tissue specimen 50. Furthermore, the image processing unit performs A/D conversion of image data to obtain a digital image, and creates the WSI. Furthermore, the image processing unit prepares a fluorescent brightness map for use in quantitative analysis of a target biological substance based on the created WSI.

The communication unit 64 is an interface to perform data transmission and reception between the interface and an external device such as a personal computer. A user, who wants to refer to the WSI, reads the WSI stored in the database 80 to the personal computer or the like via the communication unit 64, and can observe the image on a display.

The control device 60 is connected to the display device 70.

The display device 70 includes a monitor such as a cathode ray tube (CRT) or a liquid crystal display (LCD), and displays various screens in accordance with an instruction of a display signal input from the control unit 61. In the present embodiment, the display device 70 functions as an output unit to output the captured fluorescent image or the like.

The control device 60 is further connected to the database 80. The database 80 includes, for example, a hard disk drive (HDD) and others, and stores the WSI synthesized by the image processing unit 63.

[Tissue Specimen]

Subsequently, the tissue specimen 50 will be described.

The tissue specimen 50 is a tissue section including the target biological substance, and is stained with an immune stain, and the stained tissue specimen 50 is installed on the stage 40.

(1) Target Biological Substance

The target biological substance is considered as a target of immunostaining in which a fluorescent label is used mainly for detection or quantification from a viewpoint of pathological diagnosis, and the substance is the biological substance expressed in the tissue section, especially a protein (an antigen).

An example of a typical target biological substance is a biological substance that is expressed in a cellular membrane of any type of cancer tissue and is usable as a biomarker.

(2) Immune Stain (a Bonded Body of Antibody-Fluorescent Nanoparticles)

It is preferable to use, as the immune stain, a complex to which a primary antibody and fluorescent nanoparticles are coupled indirectly, i.e., by bonding other than covalent bond in which antigen-antibody reaction or the like is used, in order to improve efficiency of the fluorescent label and suppress time elapse that causes degradation of the fluorescence, as much as possible. To simplify a staining operation, a complex obtained by directly bonding the fluorescent nanoparticles to the primary antibody or a secondary antibody is usable as the immune stain.

An example of the immune stain is [the primary antibody to the target biological substance] . . . [the antibody (the secondary antibody) to the primary antibody]~[the fluorescent nanoparticles].

A mark " . . . " indicates the bonding by the antigen-antibody reaction, and there are not any restrictions on a mode of the bonding which is indicated by "~". Examples of the mode include the covalent bond, ionic bond, hydrogen bond, coordination bond, antigen-antibody bond, biotinavidin reaction, physical adsorption, and chemical adsorption. Alternatively, the bonding may be performed via linker molecules as required.

(3) Antibody

In the primary antibody, there can be used an antibody (IgG) that specifically recognizes a protein that is the target biological substance as the antigen and bonds to the antigen. For example, when HER2 is considered as the target biological substance, anti-HER2 antibody can be used, and when HER3 is considered as the target biological substance, anti-HER3 antibody can be used, respectively.

In the secondary antibody, there can be used an antibody (IgG) that specifically recognizes the primary antibody as the antigen and bonds to the antigen.

Each of the primary antibody and the secondary antibody may be a polyclonal antibody, and a monoclonal antibody is preferable from a viewpoint of stability of the quantification. There are not any restrictions on a type of animal (an immune animal) which produces the antibody, and similarly to a conventional method, the animal may be selected from the group consisting of a mouse, a rat, a guinea pig, a rabbit, a goat, and a sheep.

(4) Fluorescent Nanoparticles

The fluorescent nanoparticles are nanosized particles that are irradiated with the excitation light to emit the fluorescence, and the particles can emit the fluorescence having a sufficient intensity to represent each molecule of the target biological substance as a bright spot.

In the present invention, fluorescent substance integrated nanoparticles (PID: phosphor integrated dot nanoparticles) are used as the fluorescent nanoparticles.

(4.2) Fluorescent Substance Integrated Nanoparticles

The PID indicates nanosized particles having a structure in which particles including an organic substance or an inorganic substance constitute a mother body, and a plurality of fluorescent substances (e.g., the above quantum dots, organic fluorescent dyestuffs, etc.) are enclosed in the body and/or adsorbed on the surface of the body. As the PID, quantum dot integrated nanoparticles, fluorescent dyestuff integrated nanoparticles or the like are used.

It is preferable that the fluorescent substance for use in the PID indicates emission of visible to near-infrared light having a wavelength in a range of 400 to 900 nm, when irradiated with ultraviolet to near-infrared light having a wavelength in a range of 200 to 700 nm. It is preferable that the mother body and the fluorescent substance have substituents or parts having mutually opposite charges and that electrostatic interaction works.

There are not any restrictions on an average particle diameter of the PID for use in the present invention, but the nanoparticles having an average particle diameter of about 30 to 800 nm can be used. When the average particle diameter is less than 30 nm, less fluorescent substances are included in the integrated particles, and it becomes difficult to quantitatively evaluate the target biological substance. When the average particle diameter is in excess of 800 nm, it becomes difficult to bond to the target biological substance in a pathological tissue. Note that it is more preferable that the average particle diameter is in a range of 40 to 500 nm. Here, the average particle diameter is set to be from 40 to 500 nm. When the average particle diameter is less than 40 nm, an expensive detection system is required, and when the average particle diameter is in excess of 500 nm, a quantification range is narrowed due to a physical size.

Note that there are not any restrictions on a coefficient of variation (=(standard deviation/average value)×100%) indicating a variation of a particle diameter, but it is preferable to use the particles having a coefficient of variation which is less than or equal to 15%. When the variation of the particle diameter decreases, a variation of brightness of a fluorescent bright spot decreases. Therefore, an amount of the target biological substance to be expressed can be quantitatively evaluated on the basis of a fluorescent brightness as described later. To obtain the average particle diameter, an electron microscope photograph is taken by using a scanning electron microscope (SEM), and cross-sectional areas of a sufficient number of particles are measured. When each measured value is considered as an area of a circle, a diameter of the circle can be obtained as the particle diameter.

(4.1.1) Mother Body

Examples of the organic substance of the mother body can include resins generally classified as thermosetting resins, such as a melamine resin, an urea resin, an aniline resin, a guanamine resin, a phenol resin, a xylene resin, and a furan resin; resins generally classified as thermoplastic resins, such as a styrene resin, an acrylic resin, an acrylonitrile resin, an AS resin (an acrylonitrile-styrene copolymer), and an ASA resin (an acrylonitrile-styrene-methyl acrylate copolymer); another resin such as polylactic acid; and polysaccharide.

Examples of the inorganic substance of the mother body can include silica and glass.

(4.1.2) Quantum Dot Integrated Nanoparticles

The quantum dot integrated nanoparticles have a structure in which the above quantum dots are enclosed in the above mother body, and/or adsorbed on the surface of the mother body.

When the quantum dots are enclosed in the mother body, the quantum dots may only be dispersed in the mother body, and may be or may not be chemically bonded to the mother body itself.

As the quantum dots, there are used semiconductor nanoparticles containing II-VI group compound, III-V group compound or IV group element. Examples of the compound or element can include CdSe, CdS, CdTe, ZnSe, ZnS, ZnTe, InP, InN, InAs, InGaP, GaP, GaAs, Si, and Ge.

The above quantum dot may be used as a core on which a shell is provided. Such a quantum dot may also be used. Hereinafter, as a notation of the quantum dot having the shell in the present description, when the core is CdSe and the shell is ZnS, CdSe/ZnS is represented. For example, CdSe/ZnS, CdS/ZnS, InP/ZnS, InGaP/ZnS, Si/SiO$_2$, Si/ZnS, Ge/GeO$_2$, Ge/ZnS or the like can be used, but these examples are not restrictive.

There may be used a quantum dot subjected to a surface treatment with an organic polymer or the like as necessary. Examples of the quantum dot can include CdSe/ZnS having a surface carboxyl group (manufactured by Invitrogen Corporation) and CdSe/ZnS having a surface amino group (manufactured by Invitrogen Corporation).

It is possible to prepare the quantum dot integrated nanoparticles by a known method. For example, silica nanoparticles enclosing the quantum dots can be synthesized with reference to synthesis of CdTe enclosing silica nanoparticles which is described in New Journal of Chemistry, vol. 33, page 561 (2009).

Silica nanoparticles coated with the quantum dots can be synthesized with reference to synthesis of silica nanoparticles having surfaces on which particles of CdSe/ZnS capped with 5-amino-1-pentanol and APS are integrated as described in Chemical Communications, page 2670 (2009).

Polymer nanoparticles enclosing the quantum dots can be prepared by using an impregnation method of the quantum dots into polystyrene nanoparticles as described in Nature Biotechnology, vol. 19, page 631 (2001).

(4.1.3) Fluorescent Dyestuff Integrated Nanoparticles

The fluorescent dyestuff integrated nanoparticles have a structure in which fluorescent dyestuffs are enclosed in the above mother body, and/or adsorbed on the surface of the mother body.

Examples of the fluorescent dyestuffs can include organic fluorescent dyestuffs such as rhodamine dye molecules, squarylium dye molecules, cyanine dye molecules, aromatic ring system dye molecules, oxazine dye molecules, carbopyronine dye molecules, and pyrromethene dye molecules.

Specifically, there can be used Alexa Fluor (registered trademark, manufactured by Invitrogen Corporation) dye molecules, BODIPY (registered trademark, manufactured by Invitrogen Corporation) dye molecules, Cy (registered trademark, manufactured by GE Healthcare Co.) dye molecules, HiLyte (registered trademark, manufactured by Anaspec, Inc.) dye molecules, DyLight (registered trademark, manufactured by Thermo Scientific Co.) dye molecules, ATTO (registered trademark, manufactured by ATTO-TEC GmbH) dye molecules, MFP (registered trademark, manufactured by MoBiTec GmbH) dye molecules, CF (registered trademark, manufactured by Biotium Inc.) dye molecules, DY (registered trademark, manufactured by DYOMICS GmbH) dye molecules, CAL (registered trademark, manufactured by BioSearch Technologies Inc.) dye molecules, or the like.

Note that when the fluorescent dyestuffs are enclosed in the main body, the fluorescent dyestuffs may only be disposed in the mother body, and may be or may not be chemically bonded to the mother body itself.

It is possible to prepare the fluorescent dyestuff integrated nanoparticles by a known method. For example, silica nanoparticles enclosing the fluorescent dyestuffs can be synthesized with reference to synthesis of FITC enclosing silica particles described in Langmuir, vol. 8, page 2921 (1992). Various fluorescent dyestuff integrated nanoparticles can be synthesized by using desired fluorescent dyestuffs in place of FITC.

Polystyrene nanoparticles enclosing the fluorescent dyestuffs can be prepared by using a copolymerization method in which organic dyestuffs having a polymerizable functional group are used as described in U.S. Pat. No. 4,326,008 (1982), or an impregnation method of the fluorescent dyestuffs into the polystyrene nanoparticles as described in U.S. Pat. No. 5,326,692 (1992).

(5) Staining Method of Tissue Section

One example of a staining method will be described.

There are not any restrictions on a preparation method of the tissue section (also referred to simply as "section" including a section such as a pathological section) to which this staining method is applicable, and a section prepared by a known procedure can be used.

(5.1) Specimen Preparation Step (5.1.1) Deparaffinization Treatment

The section is immersed into a container in which xylene is placed, and paraffin is removed. There are not any restrictions on a temperature, and the immersion can be performed at room temperature. It is preferable that an immersion time is three minutes or more and 30 minutes or less. Furthermore, xylene may be changed in a middle of the immersion as necessary.

Next, the section is immersed into a container in which ethanol is placed, and xylene is removed. There are not any restrictions on a temperature, and the immersion can be performed at room temperature. It is preferable that an immersion time is three minutes or more and 30 minutes or less. Furthermore, ethanol may be changed in the middle of the immersion as necessary.

The section is immersed into a container in which water is placed, and ethanol is removed. There are not any restrictions on a temperature, and the immersion can be performed at room temperature. It is preferable that an immersion time is three minutes or more and 30 minutes or less. Furthermore, water may be changed in the middle of the immersion as necessary.

(5.1.2) Activation Treatment

An activation treatment of the target biological substance is performed, following a known method.

Activation conditions are not especially determined, and as an activation solution, there can be used a buffer solution (pH 6.0) containing 0.01 M of citric acid, a solution (pH 8.0) containing 1 mM of EDTA, 5% of urea, a buffer solution containing 0.1 M of tris hydrochloric acid, or the like.

In accordance with the tissue section for use, pH conditions are selected from a pH range of 2.0 to 13.0 to such an extent that a signal is issued and tissue roughness can be evaluated by the signal. The treatment is usually performed in a pH range of 6.0 to 8.0, and a special tissue section can be treated, for example, at pH 3.0.

As heating equipment, an autoclave, a microwave, a pressure pot, a water bath or the like can be used. There are not any restrictions on a temperature, and the treatment can be performed at room temperature. The treatment can be performed at a temperature in a range of 50 to 130° C. for a time of five to 30 minutes.

Next, the section subjected to the activation treatment is immersed into a container in which PBS is placed, and washing is performed. There are not any restrictions on a temperature, and the immersion can be performed at room temperature. It is preferable that an immersion time is three minutes or more and 30 minutes or less. Furthermore, PBS may be changed in the middle of the immersion as necessary.

(5.2) Immunostaining Step

In an immunostaining step, to stain the target biological substance, a solution of the immune stain is placed on the section, and reacted with the target biological substance. The immune stain contains fluorescent nanoparticles having a part directly or indirectly bondable to the target biological substance. The solution of the immune stain for use in the immunostaining step may be prepared in advance prior to this step.

Note that when a plurality of target biological substances are to be detected, immunostaining is performed by using a plurality of immune stains corresponding to the target biological substances. The plurality of immune stains for use in this case may only contain at least one of the immune stains in which PID is used (PID stains). When the antibody and the fluorescent substance (a fluorescent wavelength) are different from each other, it is possible to detect the plurality of target biological substances by multiplied staining with a plurality of PID stains, or multiplied staining with a combination of the PID stain and the immune stain in which the fluorescent label, such as the organic fluorescent substance or the quantum dots, is used. In this case, respective solutions of the respective immune stains are prepared, and each solution is placed on the section, and reacted with the target biological substance. When the solution is placed on the section, the respective solutions of the immune stains may be mixed in advance or may be successively placed separately.

When the plurality of immune stains are used, it is preferable that an excitation/emission wavelength of PID is away from an excitation/emission wavelength of the fluorescent label of the other immune stain to such an extent that crosstalk can be ignored.

Conditions on which the immunostaining step is performed, that is, a temperature and immersion time when immersing the tissue section into the solution of the immune stain can be appropriately adjusted so that an appropriate signal can be obtained, in conformity with a conventional immunostaining method.

There are not any restrictions on the temperature, and the immersion can be performed at room temperature. It is preferable that a reaction time is 30 minutes or more and 24 hours or less.

It is preferable to drop a known blocking agent such as PBS that contains BSA, or a surfactant such as Tween 20 before the above described treatment is performed.

(5.3) Specimen Post-Treatment Step

After the immunostaining step of the tissue specimen is finished, it is preferable that treatments such as immobilization, dehydration, clearing and sealing are performed to obtain the specimen suitable for observation.

In the immobilization and dehydration treatments, the tissue section may be immersed into a fixing solution (a crosslinking agent such as formalin, paraformaldehyde, glutaraldehyde, acetone, ethanol, or methanol). After the immobilization and dehydration treatments are finished, the tissue section may be immersed into a clearing solution (xylene or the like) in the clearing treatment. After the clearing treatment is finished, the tissue section may be immersed into a sealing solution in the sealing treatment.

Conditions on which these treatments are performed, for example, a temperature and immersion time when immersing the tissue section into a predetermined treatment solution can be appropriately adjusted so that an appropriate signal can be obtained, in conformity with the conventional immunostaining method.

(5.4) Bright Field Form Observation Staining Step

Separately from the immunostaining step, form observation staining is performed so that forms of a cell, a tissue, an internal organ and the like can be observed in a bright field of view.

The form observation staining step can be performed according to the conventional method.

As for the form observation of the tissue specimen 50, there is standardly used staining by use of eosin with which a cytoplasm, stroma, various fibers, red blood cells, and keratinocytes are stained in red to dark red. There is also standardly used staining by use of hematoxylin with which a nucleus, a lime part, a cartilage tissue, a germ and mucus are stained in livid to pale blue (a method in which these two types of staining are simultaneously performed is known as hematoxylin and eosin staining (HE staining)). In the present embodiment, it is considered that the form observation staining is performed by the HE staining method. In an image of this HE staining, the cells look stained in red and the like, and an outline of each cell can be perceived. Therefore, it is possible to also obtain information indicating a size of the cell, a size of the nucleus a number of nuclei, a stage of a cell cycle, a degree of canceration, nature of a cell population, and a relation between the populations. Furthermore, such information can be obtained in more detail by the immunostaining method. That is, a staining method obtained by combining the HE staining method and the immunostaining method can be used in the form observation staining step. In general, an image is acquired at a high magnification for observation of the target biological substance, an image is acquired at a medium magnification for specifying of a cell type and observation of an area such as a tumor area or an interstitial area, and an image is acquired at a low magnification for observation of the area or a structure of a tissue such as a blood vessel or a lymphatic vessel in each area. When all such information is acquired, stored and used in the future, whole slide is useful.

Note that when the form observation staining step is included, the step may be performed after the immunostaining step or before the immunostaining step.

[Focusing]

Subsequently, a focusing method in WSI creation will be described.

In the present embodiment, the bright field image of the tissue specimen 50 is acquired by the first image acquiring unit 20. Based on this image, an imaging region that is a WSI creation target is set, and focusing is performed on the basis of the bright field image. Furthermore, the fluorescently labeled PID of the tissue specimen 50 is irradiated with the excitation light by the second image acquiring unit 30, and stricter focusing is performed on the basis of a detected PID fluorescent bright spot.

Figure 4:
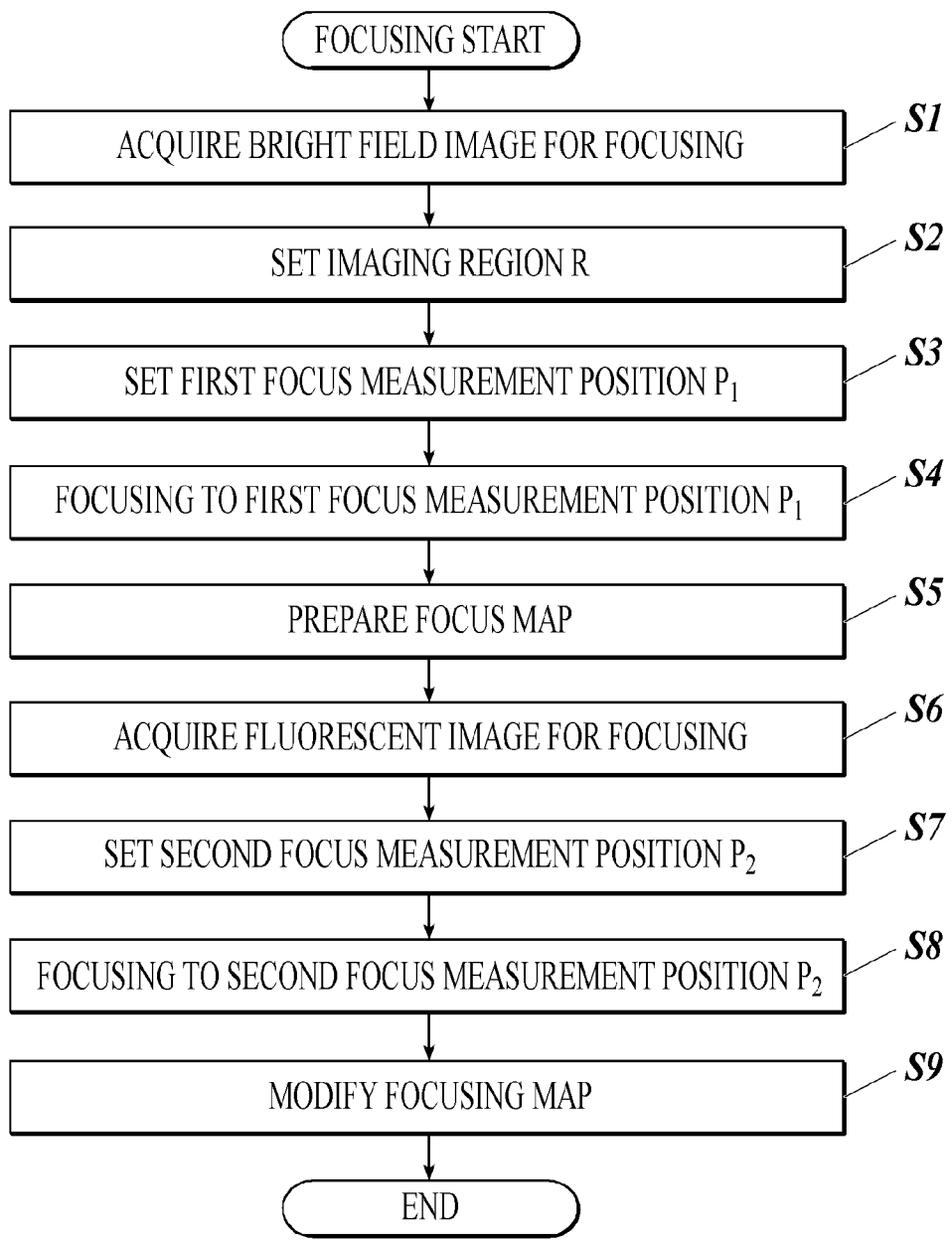
FIG. 4 is a flowchart showing control during focusing.

Specific control will be described with reference to a flowchart of FIG. 4.

Figure 5:
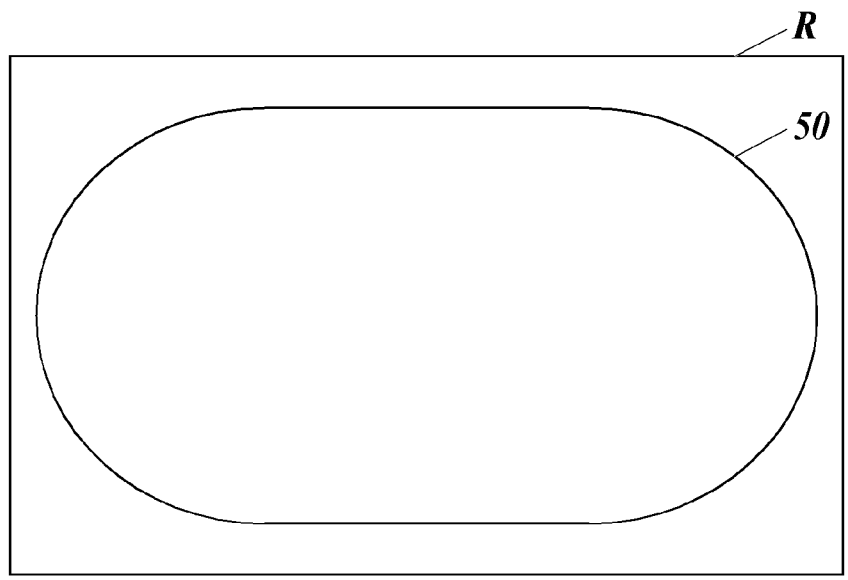
FIG. 5 is a diagram showing a setting method of an imaging region.

First, the control unit 61 controls the first image acquiring unit 20, to acquire a focusing bright field image of the whole slide glass (step S1: a bright field image capturing step). This bright field image is for use in setting conditions to capture the fluorescent image or the like at the high resolution as described later, and the image is a low magnification image obtained by using a low-magnification objective lens. Based on the obtained bright field image, the control unit 61 sets an imaging region R including the tissue specimen 50 as shown in FIG. 5 (step S2).

Specifically, the control unit 61 binarizes the entire image of the tissue specimen 50 in accordance with presence or absence of the tissue specimen 50, and detects a region where the tissue specimen 50 is present in each of an X-axis direction and a Y-axis direction, to determine the imaging region R. Note that the user may manually set the imaging region R on the display device 70, while observing the bright field image of the whole tissue specimen 50.

Next, the focusing of the tissue specimen 50 is performed based on the bright field image. The focusing based on the bright field image may be manually performed by the user, or may be automatically performed under the control of the control unit 61. Hereinafter, description will be made as to a method of automatically preparing a focus map and performing the focusing under the control of the control unit 61.

First, a first focus measurement position $P_1$ is set on the imaging region R (step S3).

Figure 6:
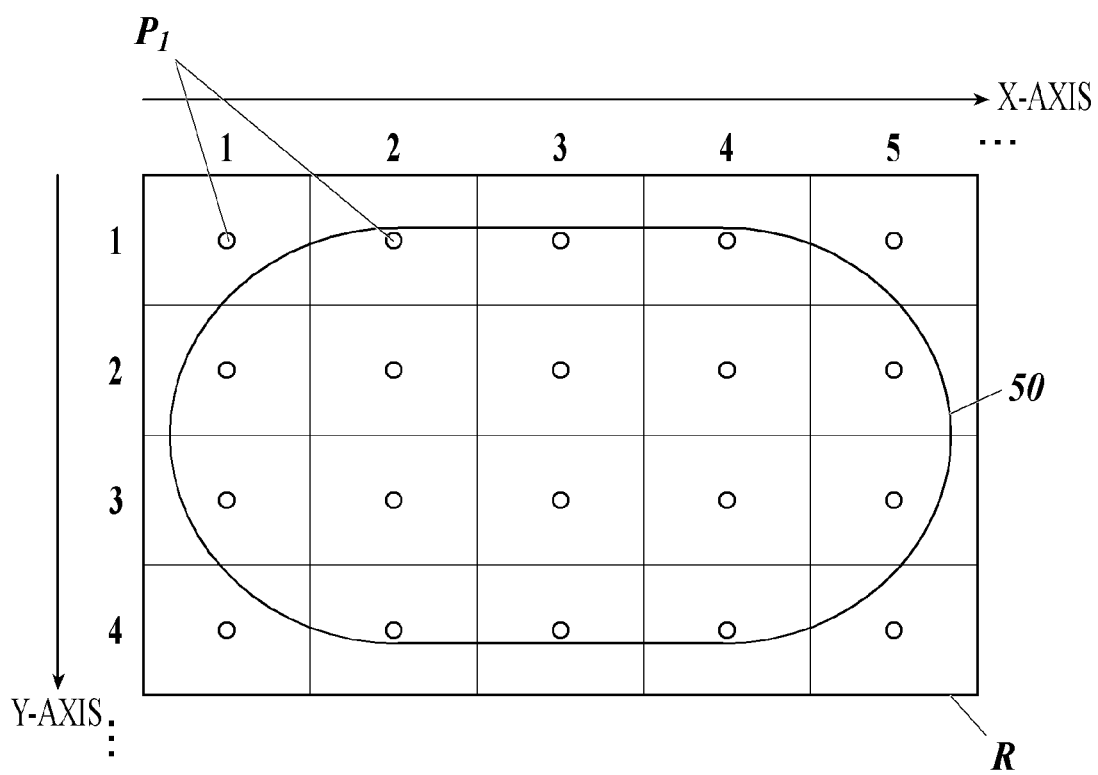
FIG. 6 is a diagram showing a setting method of a focus measurement position in a bright field image.

As shown in FIG. 6, the control unit 61 divides the imaging region R in each of the X-axis direction and the Y-axis direction to set a small region, and obtains an XY-coordinate of each small region. Here, it is considered that the XY-coordinate is a central coordinate of each small region, but this example is not restrictive. For example, a coordinate of an upper left end of each small region can be considered as the XY-coordinate.

Furthermore, as shown in FIG. 6, the control unit 61 assigns numbers 1, 2, 3, . . . to the respective small regions in each of the X-axis direction and the Y-axis direction, and sets arrangement numbers. That is, for example, the arrangement number of the small region of the upper left end of the imaging region R is (X-axis, Y-axis)=(1, 1).

Next, the control unit 61 sets the first focus measurement position $P_1$ to each small region. The position $P_1$ is considered as a central coordinate position of each small region in the present embodiment, but this example is not restrictive. For example, the upper left end of each small region can be considered as the first focus measurement position $P_1$. Furthermore, the tissue specimen 50 may not be present on the central coordinate as in the region of the arrangement number (1, 1) of FIG. 6. In this case, it is possible to move the first focus measurement position $P_1$ to an arbitrary coordinate on the tissue specimen 50.

Subsequently, the focusing is performed to the first focus measurement position $P_1$ of each small region (step S4: a specifying step). Here, the control unit 61 aligns an optical axis position with the first focus measurement position $P_1$, while moving and controlling the stage 40 in the XY-direction, to obtain a bright field focus position (a Z-coordinate) to each first focus measurement position $P_1$ by actual measurement.

Figures 7, 8:
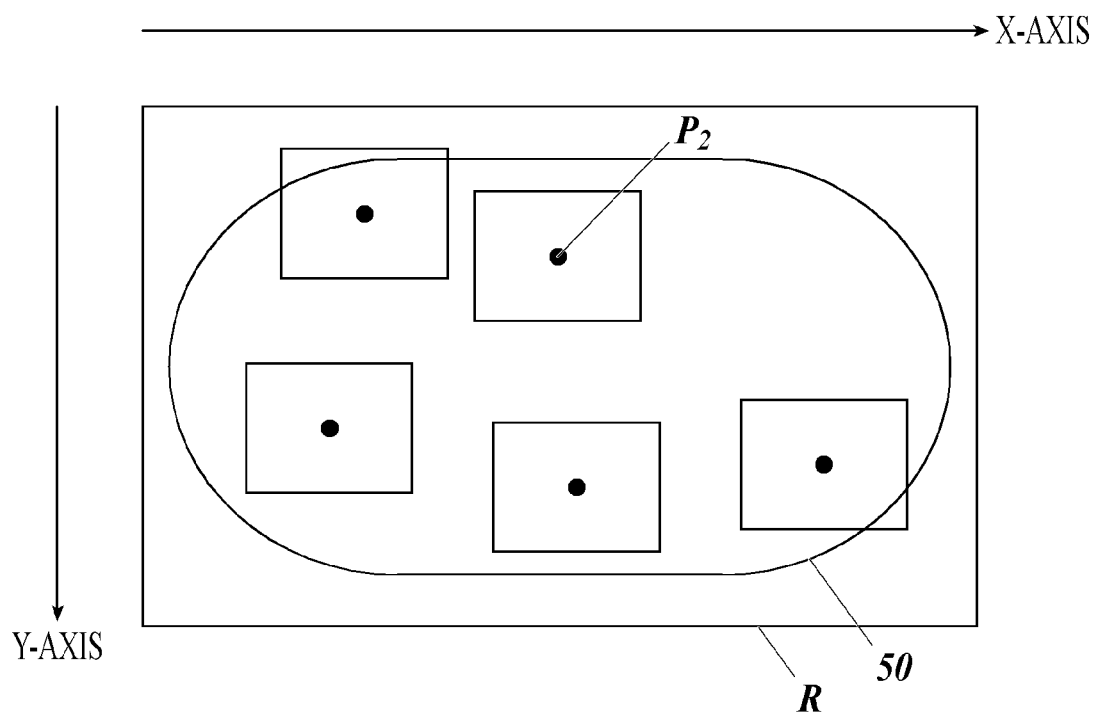
FIG. 7 is a diagram showing one example of a focus map.
FIG. 8 is a diagram showing a setting method of a focus measurement position in a fluorescent image.

The control unit 61 prepares such a focus map as shown in FIG. 7 on the basis of the bright field focus position obtained in this manner (step S5). The arrangement number of each small region and a stage coordinate corresponding to the number are stored in the focus map. The stage coordinate corresponds to the central coordinate of each small region along the X-axis or the Y-axis, and corresponds to the bright field focus position along the Z-axis.

As described above, the focusing of the tissue specimen 50 based on the bright field image is completed.

In and after step S6, focusing is performed to the PID bright spot on the basis of focusing information obtained from the bright field image. That is, as described above, the bright field focus position of the tissue specimen 50 based on the bright field image is specified by the processing of the steps S1 to S3. Furthermore, when further focusing is performed to the PID bright spot on the basis of the focus position, a more strictly focused fluorescent image can be obtained.

First, the PID fluorescent image for the focusing is acquired (the step S6: a fluorescent imaging step). That is, the control unit 61 controls the excitation light source 32 to irradiate the tissue specimen 50 with the PID excitation light, and the second imaging element 33 acquires the PID fluorescent image.

Next, an arbitrary PID fluorescent bright spot is selected from the obtained fluorescent image, and a second focus measurement position $P_2$ is set (step S7). Here, it is considered that the user manually sets the second focus measurement position $P_2$, and as shown in FIG. 8, one or more second focus measurement positions $P_2$ on the tissue specimen 50 are set.

Next, focusing is performed to the set second focus measurement position $P_2$ (step S8: a specifying step). Specifically, the control unit 61 aligns the optical axis position with the second focus measurement position $P_2$, while moving and controlling the stage 40 in the XY-direction, and makes fine adjustment in a Z-coordinate direction with reference to the focus position of the focus map prepared in the step 3, to obtain a fluorescent focus position (the Z-coordinate) to the second focus measurement position $P_2$.

When this processing is performed to all the second focus measurement positions $P_2$, the control unit 61 modifies the focus map prepared in the step S3 by use of the newly obtained focus position (step S9).

As described above, the focusing to the tissue specimen 50 is completed.

[Creation of Whole Slide Image]

When the focusing is completed as described above, the process shifts to creation of the fluorescent image of the whole tissue specimen 50, that is, the creation of the WSI.

Figure 9:
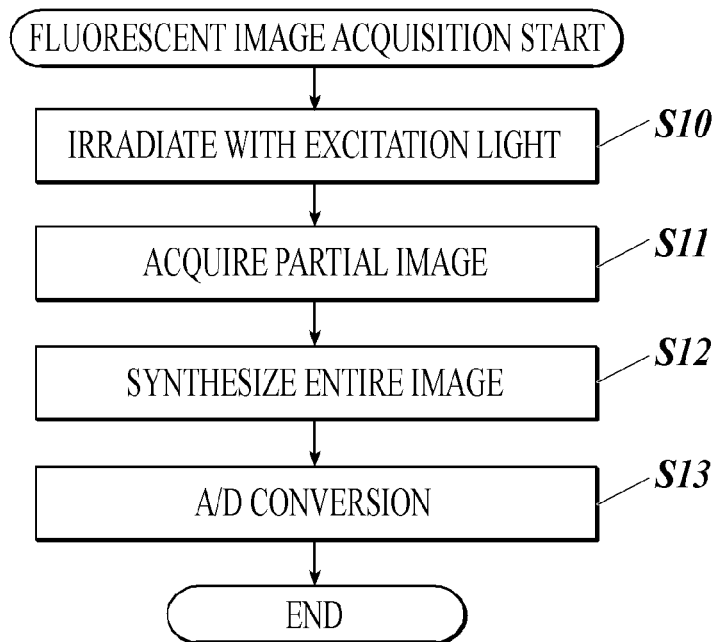
FIG. 9 is a flowchart showing control during acquisition of the fluorescent image.

Description will be made as to the WSI creation method with reference to a flowchart of FIG. 9.

First, the fluorescent label labeled in the tissue specimen 50 is excited (step S10). Specifically, the control unit 61 controls the excitation light source 32, to irradiate the tissue specimen 50 with the excitation light to excite the labeled PID.

Next, partial images of the tissue specimen 50 are acquired (step S11: a fluorescent image capturing step).

Here, based on the information of the focus map completed in the step S9, the control unit 61 moves and controls the stage 40, and controls the second image acquiring unit 30 as an image capturing unit to acquire the partial fluorescent images. That is, the optical axis position and the focus position are moved to XYZ-coordinates indicated by the stage coordinate stored in the focus map, and the second imaging element 33 as the image capturing unit is controlled to capture the image of each small region. Here, the image can be acquired at the high resolution by use of the high-magnification objective lens as the objective lens 34.

Figure 10:
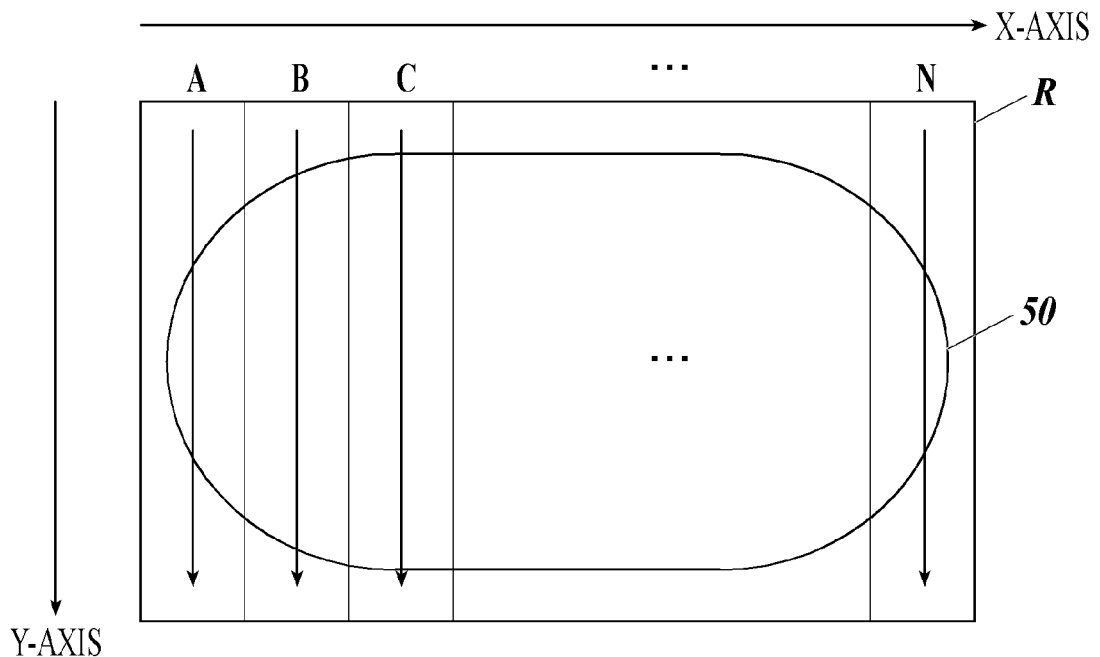
FIG. 10 is a diagram showing one example of a partial image acquiring method.

Specifically, such a belt-shaped scan image as shown in FIG. 10 is acquired as the partial image. First, the imaging is started from the upper left end of the tissue specimen 50. The control unit 61 irradiates the tissue specimen with the excitation light, and scans the specimen while moving an imaging position of the second imaging element 33 in a positive direction along the Y-axis of a tissue section 51, to acquire a partial image A. Subsequently, the control unit 61 moves the imaging position of the second imaging element 33 in a positive direction along the X-axis, to acquire a partial image B. Similarly, when the partial images are acquired in order from a partial image C, . . . to a partial image N, the imaging is completed.

Next, the control unit 61 controls the image processing unit 63 as a creating unit, and synthesizes the captured partial images, to create the whole fluorescent image of the imaging region R (step S12: a creating step). That is, the partial images A to N are arranged in the X-axis direction and pasted together, so that the whole fluorescent image of the tissue specimen 50 can be obtained at the high resolution.

Furthermore, the image processing unit 63 A/D converts the obtained whole fluorescent image of the imaging region R to obtain the digital image (step S13: a creating step). As described above, the creation of the WSI is completed.

[Use of Whole Slide Image]

The created WSI is stored by the database 80 as a storing unit (a storing step). The user, who wants to refer to the WSI, reads the image data to the personal computer or the like via the communication unit 64, and can observe the data on the display.

[High Brightness and High Light Resistance of PID]

There is a problem that a conventional fluorescent substance has a weak fluorescent brightness, and it is difficult to detect, as a bright spot, bond of the substance to the target biological substance. There is also a problem that the conventional fluorescent substance has a low light resistance and is quickly faded due to the irradiation with the excitation light during the focusing or during the fluorescent image capturing. On the other hand, the PID has a high brightness and a high light resistance, and can also withstand the creation of the fluorescent whole slide image which requires the irradiation with the excitation light for a long time.

Figure 11:
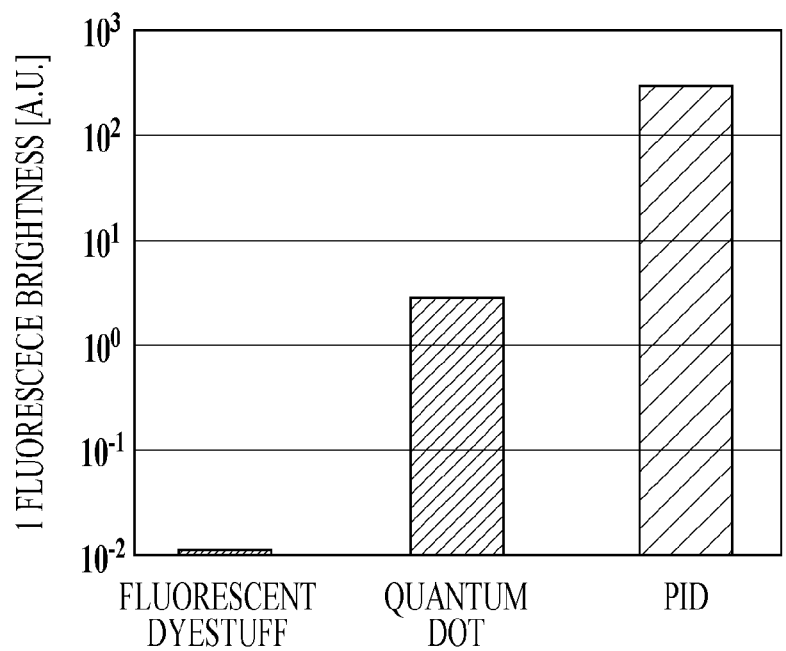
FIG. 11 is an explanatory view of a high brightness of fluorescent substance integrated nanoparticles.
Figure 12:
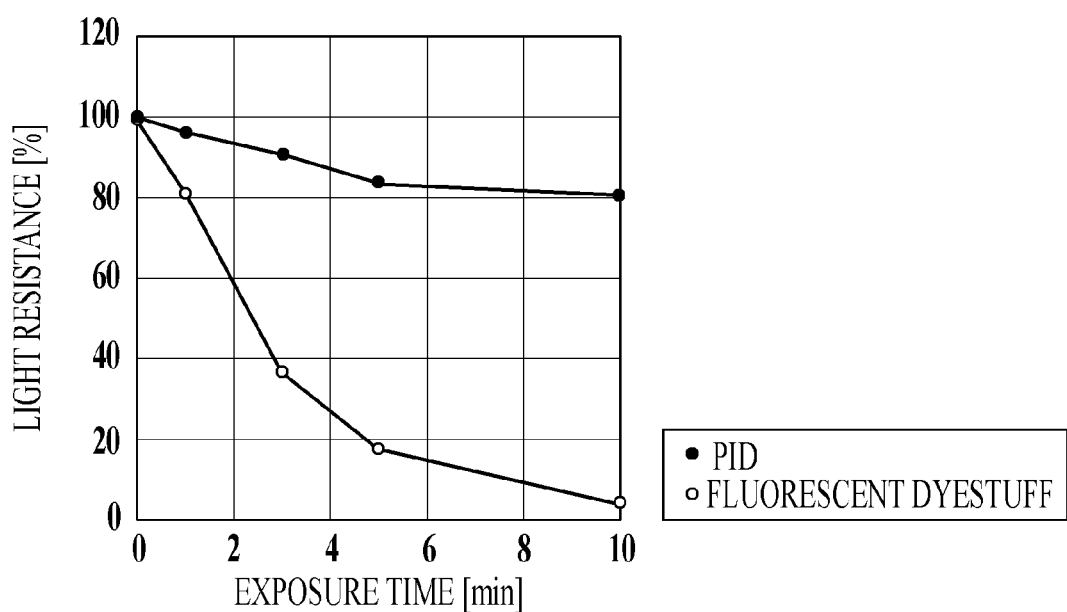
FIG. 12 is an explanatory view of a high light resistance of the fluorescent substance integrated nanoparticles.

FIG. 11 and FIG. 12 show comparison results in fluorescent brightness and light resistance among a conventional fluorescent dyestuff simple substance, a quantum dot simple substance and the PID. As shown in FIG. 11, as for the fluorescent brightness per molecule of the fluorescent label, the brightness of the PID is about 100 times as much as the brightness of the quantum dot simple substance, and is about 30000 times or more as much as the brightness of the fluorescent dyestuff simple substance. It is clear that the fluorescent brightness of the PID is noticeably improved as compared with the fluorescent dyestuff and the quantum dot.

FIG. 12 shows a difference in light resistance between the conventional fluorescent dyestuff and the PID.

In the fluorescent dyestuff, Texas Red was used, and a dyestuff concentration was adjusted to 0.33 [µM] by use of a sealing agent as a solvent. Then, the dyestuff was dropped onto a slide glass on which a tissue section was placed, and cover glass was placed over the slide glass, and left to stand in a dark place for two hours. For the PID, a dyestuff concentration was adjusted in a range of 0.001 to 0.01 [nM], and the PID was dropped onto the slide glass on which the tissue section was placed, and left to stand in a dark place for 10 minutes. Afterward, washing and coating with a sealing agent were performed, and cover glass was placed, to create a tissue specimen.

These tissue specimens were irradiated with excitation light having an excitation wavelength of 580 nm and an excitation light intensity of 20 to 30 mW, and the light resistances were observed.

As shown in FIG. 12, a fluorescent brightness at start of exposure was set to 100%, and a change of the fluorescent brightness over time was represented by the light resistance.

In case of the fluorescent dyestuff, the light resistance was below 10% after elapse of 10 minutes from the exposure start, while in case of the PID, a light resistance of 80% was maintained even after elapse of 10 minutes from the exposure start. Therefore, it is clear that the fluorescent bright spot at the start of the exposure has a sufficiently observable fluorescent brightness even after the elapse of 10 minutes from the exposure start.

As described above, the PID has a higher brightness and a higher light resistance than the heretofore used simple fluorescent substance, and hence, fluorescent observation can be performed at a high sensitivity. That is, it can be considered that the PID is applicable even to a case where much time is required for the focusing and fluorescent image capturing and a time for the irradiation of the fluorescent label with the excitation light lengthens as in the WSI creation.

[Quantitative Analysis]

Next, description will be made as to a quantitative analysis method of the target biological substance in an image processing system to which the present invention is applied.

As described above, the PID fluorescent bright spot has the high brightness, and the bright spots can be individually detected. Therefore, expression of the target biological substance can be detected as the bright spot (a detection step).

FIG. 13 shows a number of bright spots per cell which is measured. A sensitivity of detection of the target biological substance by each of the PID and the fluorescent dyestuff is measured as the number of the bright spots.

In immunostaining, a human breast tissue was stained by using an immune stain in which an anti-human ER antibody was used. Note that as the PID, there were used silica nanoparticles enclosing Cy5 (an average particle diameter of 103 nm), silica nanoparticles enclosing tetramethylrhodamine (an average particle diameter of 104 nm), or silica nanoparticles enclosing FITC (an average particle diameter of 106 nm). As the fluorescent dyestuff, each of Cy5, tetramethylrhodamine, and FITC was used in a simple substance as a fluorescent label. A tissue section stained with each immune stain was observed by using a fluorescent microscope, and the number of the fluorescent bright spots was measured.

Note that a spot number indicates a difference in stain concentration, and spot number 8 indicates the highest concentration.

In FIG. 13, "−" indicates that there are not any bright spots having a background level or more, and "+" indicates that a bright spot has such a high emission intensity that the bright spot cannot be distinguished from surrounding bright spots.

It is seen from FIG. 13 that, when the tissue is stained by using the fluorescent dyestuff simple substance, there are not any bright spots having the background level or more in tissue sections having spot numbers 1 to 4. In tissue sections having spot numbers 5 to 8, the bright spot cannot be distinguished from the surrounding bright spots, and hence, the bright spot level to a slight amount of the target biological substance cannot be quantitatively evaluated.

On the other hand, when the PID is used as the label, even the slight amount of the target biological substance can be quantitatively detected with high accuracy.

Consequently, it is clear that, according to the fluorescent staining by use of the PID, an expression level of the target biological substance per cell can be quantitatively evaluated as compared with the fluorescent staining by use of the conventional fluorescent dyestuff simple substance. That is, according to the image processing system in the present invention, the fluorescent image of the whole tissue specimen can be acquired. Consequently, it is possible to quantitatively evaluate the expression level of the target biological substance in the whole tissue specimen by use of the above described detection method.

In consequence, according to the image processing system in the present invention, quantification of the target biological substance to more cells can be performed by using one image, and highly reliable quantitative evaluation results can be obtained.

Furthermore, the fluorescent brightness map with which an amount of the target biological substance to be expressed can be confirmed at a glance can be prepared by using the PID fluorescent image (a detection step).

In case of the staining with the conventional simple fluorescent substance, it is difficult to prepare the fluorescent brightness map, for example, because the fading occurs during the focusing or during the whole image capturing, variation of the brightness of the fluorescent substance is large, or a dense region of the fluorescent dyestuff does not necessarily match a high expression region of the target biological substance.

On the other hand, as described above, the PID hardly fades during the focusing or during the whole image capturing, and the variation of the fluorescent brightness per particle is small.

In FIG. 14, an ordinate indicates a frequency (a ratio to the number of all the bright spots or the number of the bright spots), and an abscissa indicates a brightness integrated value. There is shown a brightness distribution of fluorescent bright spots when a coefficient of variation of PID particle diameters is 5%. Note that the brightness integrated value is a value obtained, for example, by extracting, from the fluorescent image, a bright spot region around the fluorescent bright spot, dividing the bright spot region into a plurality of fluorescent images in the X-axis direction and the Y-axis direction to prepare small divisions, calculating the brightness of each small division, and integrating brightness values of all the small divisions. As shown in FIG. 14, the brightness integrated value indicates a distribution curve having a shape close to a shape of t-distribution, and the curve has a peak in the vicinity of a brightness integrated value of $3.5 \times 10^6$ in this case. That is, it is seen that the variation of the fluorescent brightness per particle of the PID is small.

From such PID characteristics, it is possible to consider the region having the high fluorescent brightness as the highly expressed region of the target biological substance, and hence, a fluorescent brightness map can be prepared as follows.

First, a tissue specimen is stained by using PID, to create WSI. The created WSI is read in image processing software, and intensity of fluorescent brightness is represented by light and shade of color, so that the fluorescent brightness map can be displayed. More specifically, the control unit 61 calculates an average value of the fluorescent brightness for each predetermined pixel, reads a set value of concentration of the color corresponding to the fluorescent brightness which is stored in the storage unit 62, and associates the average value with this set value, to perform image processing of the WSI. Note that a pixel unit can be arbitrarily designated by the user.

Figure 15A:
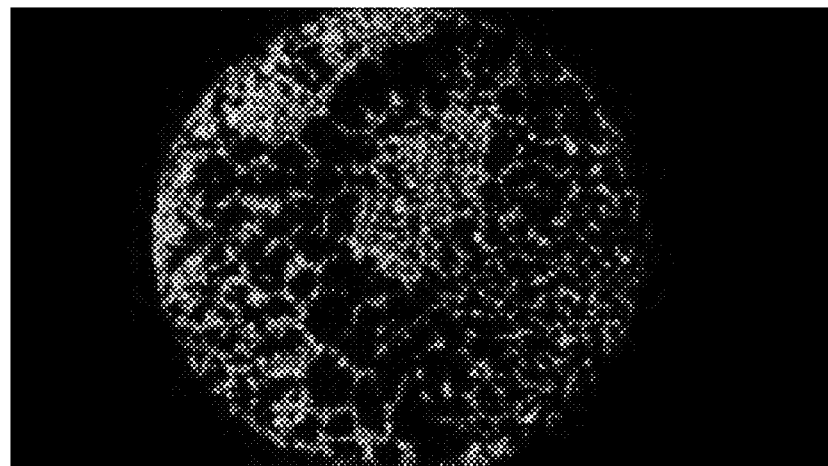
FIG. 15A is a view showing one example of a fluorescent brightness map to which the present invention is applied.
Figure 15B:
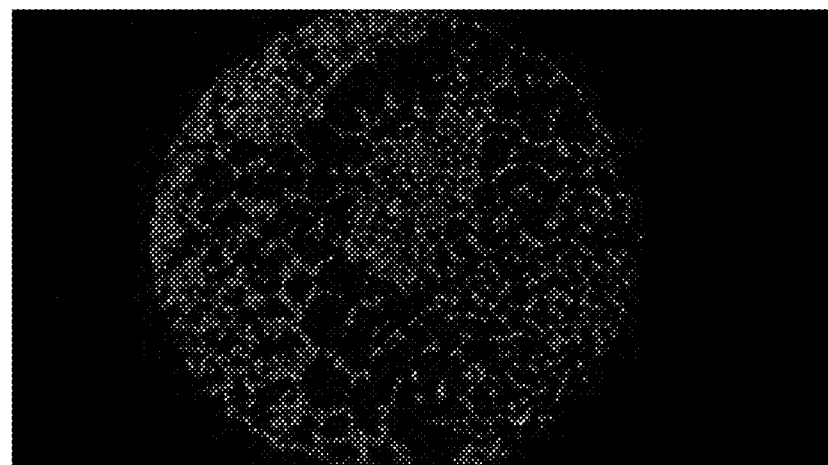
FIG. 15B is a view showing that 50 pixels are averaged in the fluorescent brightness map of FIG. 15A.
Figure 15C:
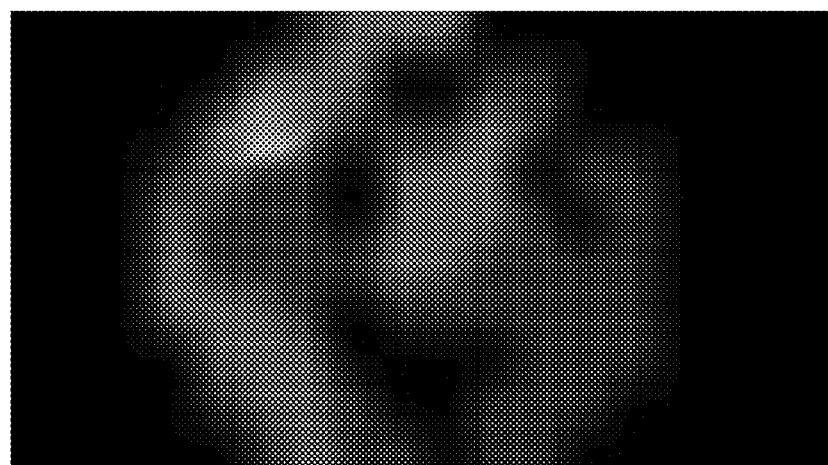
FIG. 15C is a view showing that 1000 pixels are averaged in the fluorescent brightness map of FIG. 15A.

FIG. 15 shows one example of the fluorescent brightness map. FIG. 15A shows a fluorescent image of a tissue microarray stained with the PID. The light and shade of the color of the fluorescent brightness map do not have to be displayed for each pixel. For example, the light and shade of the color may be averaged for 50 pixels or 1000 pixels, and displayed. FIG. 15B shows a fluorescent brightness map prepared from the average of 50 pixels, and FIG. 15C shows a fluorescent brightness map prepared from the average of 1000 pixels. At a glance of such a fluorescent brightness map, a region where a large amount of target biological substance is expressed can be visually selected from the WSI of the whole tissue specimen.

Furthermore, in the above embodiment, there has been described the method of staining all the cells on the tissue specimen 50 by use of the HE staining method. However, when form observation is performed by using a staining agent with which a cell type, a region, a tissue structure or the like is recognizable, it is possible to perform the quantitative analysis for each cell type.

For example, when the tissue specimen 50 is stained by using a plurality of staining agents with which only a specific cell can be stained, the quantitative analysis of the target biological substance can be performed for each cell type. In particular, it is considered that quantitative analysis of expression of target substances of microphages, T-cells, B-cells or dendritic cells that are known as immune cells can produce detailed medical records of an immune status of a patient, and becomes involved in establishment of cancer immunotherapy. Examples of the target biological substance in this case can include CD163, CD204, CD68, Iba1, CD11c, CD206, CD80, CD86, CD163, CD206, CD181, CD197, iNOS, Arginase 1, CD38, and Egr2.

[Effect]

According to the present invention, it is possible to create a fluorescent whole slide image which could not be created by staining with a heretofore used simple fluorescent substance. That is, it is possible to perform quantitative evaluation of expression of a target biological substance associated with a whole tissue specimen, by use of the fluorescent whole slide image of PID.

Furthermore, a bright field image is obtained as a cell form image in which a cell type, a region and a cell structure that are to be observation targets are only visualized, or a cell form image in which these images are combined and visualized, to construct the WSI. Additionally, the WSI of a fluorescent image in which the target biological substance is stained with the PID is constructed. Consequently, in addition to heretofore performed analysis of specifying of the cell type or the like, measuring of a number of cells or the like by use of the bright field image, quantitative analysis of expression of the target biological substance for each cell type can be performed. Therefore, it is considered that an analysis technique according to the present invention becomes noticeably useful for future clinical support and drug development.

Other Embodiments

The present invention has been specifically described above on the basis of the embodiment, but the above embodiment is one preferred example of the present invention, and the present invention is not limited to this embodiment.

For example, in the above embodiment, it is explained that the focus position is specified on the basis of the bright field image, and the focus position is modified on the basis of the fluorescent image to perform the focusing. However, the focusing may be performed by using the fluorescent image without using the bright field image. That is, a sufficient number of PID bright spots to specify the focus position of the whole tissue specimen may be selected as focus measurement positions, to perform the focusing. Also in this case, effects of the present invention can be obtained.

Furthermore, in the above embodiment, it is explained that the bright field image and the fluorescent image are captured by the first imaging element 22 and the second imaging element 33, respectively, that is, the different imaging elements are used. However, the same imaging element may be used.

In the above embodiment, it is explained that the second imaging element 33 is the imaging element, such as the one-dimensional CCD camera, that can acquire the one-dimensional image or the two-dimensional image in the longitudinal direction that is the predetermined direction. However, when the same imaging element is used, for example, a two-dimensional CCD sensor that can acquire a rectangular two-dimensional image is used as the imaging element, and obtained rectangular fluorescent images are pasted together so that the WSI can be created.

Additionally, in the above embodiment, it is explained that the tissue specimen is stained in the multiplied manner with the plurality of immune stains containing the PID stain, but the present invention is not limited to this embodiment. A single PID stain can be used.

In addition, it is explained in the above embodiment that the imaging region is set on the basis of the bright field image, but the present invention is not limited to this embodiment. The setting may be performed on a basis of a dark field image. In this case, it is considered that the first image acquiring unit has a dark field light source.

Furthermore, in the above embodiment, it is explained that the focusing to the bright field image is automatically performed, but the user may manually perform the focusing. In this case, the user sets the first focus measurement position P$_1$ to an arbitrary coordinate, so that focus of a concerned region can be more selectively adjusted.

Additionally, in the above embodiment, it is explained that the tissue section as the biological sample is used as the target and the tissue specimen 50 is stained with the immune stain containing the fluorescent substance integrated nanoparticles as the fluorescent label. The target of the biological sample may be a cultured cell or a gene (DNA).

In addition, the detailed configurations of the respective devices and the detailed operations of the respective devices that constitute the image processing system 1 can be suitably changed without departing from the gist of the present invention.

INDUSTRIAL APPLICABILITY

The present invention can be used in an image processing method and an image processing system.

REFERENCE SIGNS LIST 1 image processing system
10 microscope device
20 first image acquiring unit
21 bright field light source
22 first imaging element
30 second image acquiring unit (an image capturing unit)
31 transmission light source
32 excitation light source
33 second imaging element
40 stage
50 tissue specimen
60 control device
61 control unit
62 storage unit
63 image processing unit (a creating unit)
64 communication unit
70 display device
80 database (a storing unit)

The invention claimed is:

1. An image processing method comprising:
specifying a focus position of a fluorescent image of a fluorescently labeled tissue specimen;
capturing the fluorescent image;
creating a fluorescent whole slide image based on the captured fluorescent image; and
storing the created fluorescent whole slide image,
wherein the tissue specimen is fluorescently labelled by using, as a staining reagent, fluorescent substance integrated nanoparticles obtained by bonding a biological substance recognition part to fluorescent particles on which a plurality of fluorescent substances are integrated, and the fluorescent substance integrated nanoparticles have an average particle diameter of 30 to 800 nm,
in the specifying the focus position, a fluorescent bright spot of the fluorescent substance integrated nanoparticles is specified as a fluorescent focus position, and
in the capturing the fluorescent image, a focused fluorescent image is captured based on the fluorescent focus position.

2. The image processing method according to claim 1 comprising:
capturing a bright field image of the tissue specimen,
wherein in the specifying the focus position, an arbitrary coordinate on the bright field image is specified as a bright field focus position, and
in the capturing the fluorescent image, the focused fluorescent image is captured based on the bright field focus position and the fluorescent focus position.

3. The image processing method according to claim 1, wherein the tissue specimen is fluorescently labelled in a multiplied manner by use of the staining reagent in which the fluorescent substance integrated nanoparticles are used, and another staining reagent.

4. The image processing method according to claim 3, wherein an excitation wavelength and an emission wavelength of the fluorescent substance for use in the other staining reagent do not overlap with an excitation wavelength and an emission wavelength of the fluorescent substance that the fluorescent substance integrated nanoparticles have, respectively.

5. The image processing method according to claim 1 comprising:
detecting a biological substance in the fluorescently labelled tissue specimen, wherein an expression level of the biological substance is obtained by measuring a number of bright spots.

6. The image processing method according to claim 1 comprising:
detecting a biological substance in the fluorescently labelled tissue specimen, wherein an expression level of the biological substance is displayed as a fluorescent brightness map in which intensity of a fluorescent brightness is represented by light and shade of color.

7. The image processing method according to claim 1 comprising:
capturing a bright field image of the tissue specimen, wherein the bright field image is obtained by imaging the tissue specimen stained with one or more staining agents with which a specific cell type, a specific region or a specific tissue structure is recognizable.

8. An image processing system comprising:
an image capturing unit that captures a fluorescent image of a fluorescently labelled tissue specimen,
a creating unit that creates a fluorescent whole slide image based on the fluorescent image captured by the image capturing unit, and
a storing unit that stores the fluorescent whole slide image created by the creating unit,
wherein the tissue specimen is fluorescently labelled by using, as a staining reagent, fluorescent substance integrated nanoparticles obtained by bonding a biological substance recognition part to fluorescent particles on which a plurality of fluorescent substances are integrated, and the fluorescent substance integrated nanoparticles have an average particle diameter of 30 to 800 nm,
a fluorescent bright spot of the fluorescent substance integrated nanoparticles is specified as a fluorescent focus position of the fluorescent image, and
the image capturing unit captures a focused fluorescent image based on the fluorescent focus position.

* * * * *